(12) United States Patent
Kling et al.

(10) Patent No.: US 8,568,711 B2
(45) Date of Patent: Oct. 29, 2013

(54) ANTIMICROBIAL COMPOSITIONS

(75) Inventors: William O. Kling, Dallas, TX (US); Eric C. Luo, Plano, TX (US)

(73) Assignee: Swiss-American Products, Inc., Carrollton, TX (US)

( * ) Notice: Subject to any disclaimer, the term of this patent is extended or adjusted under 35 U.S.C. 154(b) by 0 days.

(21) Appl. No.: 12/665,014

(22) PCT Filed: Jun. 18, 2008

(86) PCT No.: PCT/US2008/067406
§ 371 (c)(1),
(2), (4) Date: Apr. 20, 2010

(87) PCT Pub. No.: WO2008/157643
PCT Pub. Date: Dec. 24, 2008

(65) Prior Publication Data
US 2010/0203028 A1    Aug. 12, 2010

Related U.S. Application Data

(60) Provisional application No. 60/936,120, filed on Jun. 18, 2007.

(51) Int. Cl.
*A61K 38/43*    (2006.01)
*A01N 59/16*    (2006.01)

(52) U.S. Cl.
USPC .................................. 424/94.1; 424/68

(58) Field of Classification Search
USPC .................................. 424/94.1, 618
See application file for complete search history.

(56) References Cited

U.S. PATENT DOCUMENTS

| | | | |
|---|---|---|---|
| 5,607,683 A | 3/1997 | Capelli | |
| 5,744,151 A | 4/1998 | Capelli | |
| 6,716,895 B1 * | 4/2004 | Terry | 523/122 |

OTHER PUBLICATIONS

International Search Report; US/ISA (Lee W. Young, authorized officer); dated Sep. 3, 2008.
International Preliminary Report on Patentability; US/IPEA (Neil Levy, authorized officer); dated Sep. 30, 2009).

* cited by examiner

*Primary Examiner* — Karen Cochrane Carlson
*Assistant Examiner* — Natalie Moss
(74) *Attorney, Agent, or Firm* — Winstead PC

(57) ABSTRACT

An antimicrobial composition is provided having a mole ratio of equivalents of silver ion to equivalents of anion of greater than 1. The invention further relates to antimicrobial compositions composed of silver ions and silver salt particles. Also provided are methods for using the compositions of the invention for the treatment of a subject, and methods for conferring antimicrobial protection to an object.

7 Claims, No Drawings

ANTIMICROBIAL COMPOSITIONS

CROSS REFERENCE TO RELATED APPLICATIONS

This application claims benefit from U.S. Provisional Application Ser. No. 60/936,120, filed Jun. 18, 2007, which application is incorporated herein by reference.

FIELD OF THE INVENTION

The invention relates to antimicrobial compositions composed of silver ions and silver salt particles. The compositions may be used to provide antimicrobial therapy to a test subject.

BACKGROUND OF THE INVENTION

It is well known that certain preparations of silver have antimicrobial properties. Silver was employed as a germicide and an antibiotic before modern antibiotics were developed. In previous centuries, users would shave silver particles into their drinking water, or submerge whole silver pieces in the drinking water, for the purpose of ingesting the silver by drinking the water. It seems likely that the practice of eating with silver utensils (i.e., silverware) resulted from a belief in the beneficial properties of silver.

There may be many reasons why administering silver suspended in solution would enhance an individual's health. It is possible that such a solution operates to inhibit the growth of bacteria, viruses, and other unwanted organisms, as well as eradicating such existing bacteria, viruses, and other organisms, as well as having an anti-inflammatory effect.

An object of the invention describes the use of a silver composition to treat certain human ailments. An embodiment of the invention is a silver composition comprising small particles of silver salt and free silver ions.

SUMMARY OF THE INVENTION

An embodiment of the invention is achieved by providing an antimicrobial composition comprising anion; silver ion; solvent, and hydrophilic polymer wherein the mole ratio of equivalents of silver ion to equivalents of anion is greater than 1.

An embodiment of the invention further provides preparations comprising the above composition for treating infection in a subject by applying an effective amount of the composition to a region of treatment.

An embodiment of the invention provides methods of conferring antimicrobial protection to wound dressings and other objects.

DESCRIPTION OF PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved silver product with significant abilities to kill human pathogens both in vivo and in vitro.

Generally, the present invention represents a novel approach to killing or disabling microorganisms that are hazardous to human beings by the use of a composition that comprises silver salt particles and free silver ions.

An embodiment of the invention provides a composition comprising silver salt particles and free silver ions, wherein the content of silver is between 0.0001 and 0.01 mole/liter, which composition kills or disables microorganisms that are hazardous to the human body.

It should be noted that specifying the total amount of silver in a composition of particles does not completely specify the material. As the particles comprising the composition are made smaller, a given concentration of silver will represent a larger number of particles. Thus, particle size and range of particle size is an important parameter for defining an effective inventive composition.

In an embodiment of the composition of the invention, greater than 50% of the silver particles have a maximum dimension less than 5 mm. A preferred range for the size of the silver particles is 0.1 to 1.0 mm.

In an embodiment of the composition, the composition is formed by mixing a silver ion donating salt with an anion donating salt. The mixing gives rise to a composition comprising particles of silver salt in combination with silver ions.

An embodiment of the invention provides an antimicrobial composition comprising: anion donating salt; silver ion donating salt; solvent; and hydrophilic polymer, wherein the mole ratio of equivalents of silver ion donating salt to equivalents of anion donating salt is greater than 1.

A preferred ratio of equivalents of silver ion donating salt to equivalents of anion donating salt is between 1.1 to 1 and 2 to 1.

Another embodiment of the invention provides an antimicrobial composition comprising anion derived from an anion donating salt, silver ion derived from a silver ion donating salt, solvent and hydrophilic polymer, wherein the mole ratio of equivalents of silver ion to equivalents of anion is greater than 1. The higher ratio of silver ions relative to the anions in the mixture contributes to the greater efficacy of the compositions of the invention, in comparison to compositions that are known in the prior art. In certain embodiments of the invention, the composition contains particles of silver salt that are derived from the reaction between an anion donating salt and a cation donating salt.

The metal cation of this invention is silver ion. However, the teachings of this invention are applicable to the use of many other metal cations. These metal cations include all metal compounds that are physiological, antimicrobial compounds, in particular, metal compounds that are "oligodynamic". The term "oligodynamic" is used to denote a metal agent, particularly a metal salt or a metal ion it yields upon dissociation, that has antimicrobial activity in very small quantities. The "oligodynamic" metals include the precious metals, such as silver, gold and platinum, and other metals such as copper, zinc, cerium, and gallium. The preferred oligodynamic metal ion is silver ion.

The preferred concentration of silver ions in the composition is in the range of 0.00001 mole/liter to 0.0002 mole/liter.

The silver ions are derived from silver-ion donating salts such as silver nitrate, silver acetate, silver citrate, and silver sulfate.

Suitable anions include chloride, bromide, iodide and thiocyanate, the most preferred anion for physiological applications being chloride. Chloride is preferred because the chloride ion is the most abundant anion in the human body and has the lowest toxicity.

Any source of the anion may be used to provide an amount of the anion. Suitable sources of anions include the inorganic salts which are physiologically tolerable. These include, but are not limited to, sodium chloride, potassium chloride, sodium bromide, potassium bromide, calcium chloride, potassium iodide and sodium thiocyanate. The preferred sources of anions are sodium chloride, hydrochloric acid or a mixture thereof.

The amount of anions to be added to the composition will depend on the amount of metal cations in the composition and which anion is being used. The ratio of equivalents of metal cations to equivalents of anions is greater than 1.

A preferred ratio of equivalents of silver ions to equivalents of anions in the compositions of the invention is between 1.1 to 1 and 2 to 1.

A certain amount of solvent may be present in the composition according to the invention. It is used as a convenience to promote the solvation of the salts that provide the antimicrobial metal cations and the salts used to supply the anions, and these salts are usually added as solutions in the solvent. Any solvent may be used which is physiologically compatible and also compatible with the metal cations and the salts that provide the anions. The preferred solvents are alcohol, acetone, water and a mixture thereof. The most preferred solvent is water.

The amount of water to be added can be high so long as the concentrations of salt are maintained. The preferred concentration of water in the final composition is between 20% by weight and 98% by weight and most preferably between 40% and 90% by weight.

Compositions of the invention may be manufactured in the form of solutions, creams, ointments, pastes, or hydrogels. When in the form of a solution, cream, or ointment, the metal-based antimicrobial compositions of this invention can be used topically on skin, in wounds, or in body orifices for the treatment or prevention of a large number of topical infections. For the treatment or prevention of infections in wounds, the composition can be applied to the wound site by standard methods known to the industry. Wound dressings may be used in conjunction with the composition as currently practiced in the treatment of topical infections. The composition offers long term antimicrobial protection and helps prevent the desiccation of the wound site. In the treatment of eye infections, the composition can be applied to the lower eyelid of the patient using standard techniques or the composition may be in the form of an eyewash and applied using standard techniques. In the treatment of mouth infections, including gingivitis, the composition in the form of a solution or cream can be applied using an applicator or a toothbrush. The compositions of the invention may also be in the form of a solution and used for infusing into a body cavity and thereby treating infection.

Embodiments of the invention include compositions in the form of hydrogels. Such compositions have utility in topical applications, where a moist wound environment is required. Three forms are available: amorphous, impregnated-gauze, and sheet. Amorphous hydrogels come in tubes, foil packets, and spray bottles. The hydrogel in the amorphous form can vary in thickness and viscosity. An impregnated-gauze hydrogel, which is amorphous hydrogel impregnated into a gauze pad, can be used to fill in dead space in a large wound. Amorphous and impregnated-gauze hydrogels are nonadherent. A secondary dressing must be applied to keep the hydrogel in place. Sheet hydrogels consist of hydrophilic polymer matrix. The dressing can overlap intact skin and generally won't harm it. Sheet hydrogels can be cut to fit the wound and typically do not require a secondary dressing.

The compositions of this invention offer several major advantages for the topical application of metal ions to the patient. First, the compositions do not contain any antibiotics to which the patient may be sensitive. Second, the risk of having bacteria develop resistance to an antibiotic—the creation of a highly resistant strain of microbe—is substantially eliminated. Also, especially in the case of antimicrobial silver ions, the composition will not stain the patient's skin or clothes, a problem which is associated with the use of prior art metal-based compositions or metal salts.

Efficacy of Silver-Containing Composition Formulated as a Hydrogel

Modern wound care has come to recognize the fact that for optimal healing a wound should be kept sterile and protected from desiccation and environmental contaminants. Traditional bandages are effective as providing protection from environmental contaminants but are largely ineffective at preventing desiccation. Bandages may be rendered antimicrobial through the addition of a variety of disinfectant substances, but these substances are often harsh and kill cells or the body as well as microbes. In recent times wound care has been revolutionized by hydrogel materials which are available as either a semisolid (amorphous material) or as a soft sheet-like material. The hydrogel is hydrophilic and hence prevents desiccation of the wound. The sheet-like material is effective at excluding environmental contaminants and because of its hydrophilic character, the hydrogel can actually absorb excess fluid exuded by the wound.

Hydrogels are formed by combining a hydrophilic polymer with other ingredients in an aqueous solution. The amount of hydrophilic polymer used in the compositions of the invention vary from 0.3% by weight to 5% by weight. The polymer forms a gel following a change in pH, temperature or other triggering event. Although the composition may be an amorphous semi-solid or a firmer sheet-like material, the vast majority of the volume tends to be occupied by the aqueous solution as opposed to the hydrophilic polymer. Hydrophilic polymers that are appropriate for the production of hydrogels include gelatin, carboxy-methyl cellulose (and other cellulose derivatives), other carbohydrate polymers of plant or algal origin such as alginate, carrageenan, xanthan gum, locust bean gum, gum traganth, guar gum, gum arabic and other plant gums, acrylic acid polymers (such as Carbopol™ or Carbomer™), poly(vinyl alcohol), poly(vinyl pyrrolidone), glyceryl polyacrylate and hydroxypropylmethyl cellulose (HPMC), sodium carboxycelluose, carboxymethylcellulose, hydroxyethylcellulose, hydroxypropyl cellulose, and other alkylcellulose derivatives and combinations of these and similar hydrophilic polymers.

In certain embodiments of the invention, a viscosity-enhancing agent may be used in the preparation of an amorphous hydrogel composition. Examples of viscosity-enhancing agents that can be used in compositions of the invention include acrylic acid polymer (such as Carbopol™ or Carbomer™), hydroxypropylmethyl cellulose (HPMC), sodium carboxycelluose, carboxymethylcellulose, hydroxyethylcellulose, hydroxypropyl cellulose and other alkylcellulose derivatives.

The aqueous component of the hydrogels may optionally contain various additive substances that enhance the physical characteristics of the hydrogel and/or enhance wound healing. These include various vitamins, amino acids and growth factors added to enhance healing or reduce scar formation to diminish scarring. Common anesthetics such as novocaine, lidocaine and derivatives thereof can also be incorporated as additives to enhance comfort. Since keeping the wound sterile is a major goal of the dressing, various antimicrobial or disinfectant agents are advantageously included. These include organic acids such as citric acid, dilute acetic acid, benzoic acid, propionic acid and lactic acid. Alcohols such as isopropanol or ethanol are useful as are organic disinfectants including chlorinated phenolics such as "TCP" (2,4,6 trichlorophenol), biguanides, chlorhexidine (when mixed with cetrimide), chlorhexidine gluconate, and chlorhexidine acetate. Disinfectant surfactants including amphoteric surfactants and aldehydes such as formaldehyde and glutaraldehyde can be included. Halogen disinfectants including iodine, iodophores, and polyvidone-iodine are effective as are peroxides and other oxygenators such as hydrogen peroxide. Other beneficial ingredients include aluminum-zinc astringent agents, furan derivatives and quinoline derivatives such as clioquinol. As beneficial as all these antimicrobial agents may be, they all tend to suffer from the defect that they can be damaging to tissue and/or microbes can readily develop resistance to them.

In certain embodiments of the invention, the silver-containing composition according to the invention further comprises one or more active agents. In an embodiment of the invention, the one or more active agents are selected from the group consisting of antimicrobials, antibiotics, antivirals, enzymes, proteins and growth factors.

As demonstrated below, the silver composition is highly effective antimicrobially, is very gentle to human tissue and is effective against microbes that may be resistant to other types of treatments. On the one hand, the hydrogel slowly releases silver ions as it slowly mixes with wound exudate. The silver ions may be derived from the particles of silver salt formed by reaction of the silver ion donating salt with the anion donating salt. On the other hand, the hydrogel donates moisture to the tissue and simultaneously makes silver available at site. In addition, the presence of silver ions in the composition enhances the antimicrobial function of the composition.

Medical devices are a major source of infection because microbes colonize their surfaces. As a result, medical devices can act as reservoirs for microbes seeding into the patient's body thereby leading to infection. If the material of a medical device can be made infection-resistant, the safety of the medical device to the patient will be enhanced substantially. An embodiment of the invention provides a method of conferring antimicrobial protection to an object by topical application of the compositions of the inventions to the surface of the object, prior to contacting said object to a subject. An example of an object that can be treated by this method is a wound dressing.

Following are examples of compositions of the invention with possible ingredients and concentrations.

Example 1

Combine 48 kg water with 1 kg hydrophilic polymer such as Ultrez 21™, mix thoroughly, add 1 kg triethanolamine and mix to form 2% gel base.

Combine 59.984 kg water, 0.004 kg NaCl, and 0.012 kg AgNO₃, mix, add 40 kg 2% gel base, mix until a homogeneous gel is obtained.

| water | 98.384% |
|---|---|
| NaCl | 0.004% |
| silver nitrate | 0.012% |
| Triethanolamine | 0.800% |
| hydrophilic polymer | 0.800% |

Example 2

Combine 23 kg water with 1 kg hydrophilic polymer such as Carbomer™, mix thoroughly, add 1 kg triethanolamine and mix to form 4% gel base.

Combine 74.987 kg water, 0.003 kg NaCl, and 0.01 kg AgNO3, mix, add 25 kg 4% gel base, and mix until a homogeneous gel is obtained.

| water | 97.987% |
|---|---|
| NaCl | 0.003% |
| silver nitrate | 0.010% |
| hydrophilic polymer | 1.000% |
| Triethanolamine | 1.000% |

Example 3

Combine 21.5 kg water with 1 kg hydrophilic polymer such as Carbomer™, mix thoroughly, add 2.5 kg 10% NaOH and mix to form 4% gel base.

Combine 64.785 kg water, 0.003 kg NaCl, and 0.012 kg AgNO₃, mix, add 10 kg glycerin, mix, add 0.2 kg allantoin, mix, add 25 kg 4% gel base, and mix until a homogeneous gel is obtained.

| water | 88.535% |
|---|---|
| NaCl | 0.003% |
| silver nitrate | 0.012% |
| glycerin | 10.000% |
| allantoin | 0.200% |
| hydrophilic polymer | 1.000% |
| NaOH | 0.250% |

Kill Rate Study 1

Objective:

To demonstrate that the test product has the antimicrobial properties of the label claim.

Test Organisms:

Cultures of the following microorganisms are maintained as stock cultures from which working inocula are prepared. The viable microorganisms used in this test must not be more than five passages removed from the original stock culture. For purposes of the test, one passage is defined as the transfer of organisms from an established culture to fresh medium.

A. *Escherichia coli* (ATCC No. 8739, Quality Technologies, Inc.)

B. *Staphylococcus aureus* (ATCC No. 6538, Quality Technologies, Inc.)

Materials:

A. Test Tubes with closures
B. Specimen Cups
C. Pipettes, 10.0 ml and 1.0 ml serological
D. Petri dishes, culture loops, and other microbiological apparatus Media:

A. Tryptic Soy Agar with lecithin and tween 80
B. DE Neutralizing Broth
C. Sterile phosphate buffered saline Procedure:

A. Preparation of Inoculum:

1. Inoculate the surface of a suitable volume of solid agar medium from a recently grown stock culture of each of the specified microorganisms. Incubate the bacterial cultures 35° C. +/− 2° for 24-48 hours and incubate at 25° C. +/− 2° C. for an additional 2-4 days.

-continued

2. Determine the number of viable microorganisms in each millimeter of the inoculum suspensions by serial dilution in sterile phosphate buffered saline.
3. Plate dilutions of $10^{-7}$ and $10^{-8}$ for the test organisms.
4. Overlay with approximately 20 ml of 45° C. Tryptic Soy Agar with lecithin and tween 80.
5. Incubate for 24-48 hours at 35° C.+/2° C. for the aerobic organisms.
6. Incubate for an additional 2-4 days at 25° C.+/2° C.
7. Count test organisms.
8. Calculate the number of organisms as colony forming units per ml (cfu/ml) of inoculum as follows:

$$\frac{cfu/\text{ml}(0.1\ \text{ml})}{9.9\ \text{gm}} = cfu/\text{gm of product}$$

B. Preparation of Test Samples:

1. Accurately pipette or weight 9.9 ml (gm) of product into an appropriately labeled or coded test tube or specimen cup.
2. Store test samples at ambient room temperature.

C. Inoculation and Plating of Samples:

1. Aseptically transfer 0.1 mil of the test organism into the appropriately labeled 9.9 ml (gm) sample of test material. Thoroughly mix or stir all samples.
2. Allow the samples to stand for six and twenty-four hours.
3. Remove one milliletter or gram aliquots at the indicated times and transfer to 9.0 ml sterile DE Neutralizing broth.
4. Perform serial dilutions from $10^{-1}$ to $10^{-5}$ in duplicate.
5. Transfer 1.0 ml of each dilution into a 100 × 15 mm petri plate.
6. Overlay with approximately 20 ml of 45° C. Tryptic Soy Agar with lecithin and tween 80.
7. Gently swirl plates and allow solidifying.
8. Incubate plates for 24-48 hours at 35° C.+/2° C. for aerobic organisms and an additional 2-4 days at 25° C.+/2° C., D. Sample Evaluation:

1. Read plates and record results on appropriate data sheet.
2. Using the calculated inoculum concentration for each test microorganism, calculate the log reduction for each microorganism to determine kill rate.

E. Records and Reports:

1. The laboratory will maintain a permanent copy of the recorded data for a period of no less than three years.
2. A written report will be issued upon completion of the study.

Results:

| Organisms | Inoculum Level | Average | Log Reduction |
|---|---|---|---|
| E. coli 6 Hours | $7.07 \times 10^5$ | 6,000 | 2.07 |
| E. coli 24 Hours | $7.07 \times 10^5$ | No Growth | 5.85 |
| S. aureus 6 Hours | $2.02 \times 10^5$ | 2,653 | 1.88 |
| S. aureus 24 Hours | $2.02 \times 10^5$ | No Growth | 5.31 |

Under the conditions of this study, the test article demonstrated reduction of growth and killing of medically important organisms within 24 hours.

Kill Rate Study 2

Objective:

To demonstrate that the test product has the antimicrobial properties of the label claim.

Test Organisms:

Cultures of the following microorganisms are maintained as stock cultures from which working inocula are prepared. The viable microorganisms used in this test must not be more than five passages removed from the original stock culture. For purposes of the test, one passage is defined as the transfer of organisms from an established culture to fresh medium.

A. *Aspergillus niger* (ATCC No. 1604, Quality Technologies, Inc.)
B. Methicillin Resistant *Staphylococcus aureus* (ATCC No. 33591, Quality Technologies, Inc.
C. *Candida albicans* (ATCC No. 10231, Quality Technologies, Inc.)

Materials:

A. Test tubes with closures
B. Specimen Cups
C. Pipettes, 10.0 ml and 1.0 ml serological
D. Petri dishes, culture loops, and other microbiological apparatus Media:

A. Tryptic Soy Agar with lecithin and tween 80
B. De Neutralizing Broth
C. Sterile phosphate buffered saline Procedure:

A. Preparation of Inoculum:

1. Inoculate the surface of a suitable volume of solid agar medium from a recently grown stock culture of each of the specified microorganisms. Incubate the bacterial cultures 35° C. +/− 2° for 24-48 hours and incubate at 25° C. +/− 2° C. for an additional 2-4 days.
2. Determine the number of viable microorganisms in each millimeter of the inoculum suspensions by serial dilution in sterile phosphate buffered saline.
3. Plate dilutions of $10^{-7}$ and $10^{-8}$ for the test organisms.
4. Overlay with approximately 20 ml of 45° C. Tryptic Soy Agar with lecithin and tween 80.
5. Incubate for 24-48 hours at 35° C.+/2° C. for the aerobic organisms.
6. Incubate for an additional 2-4 days at 25° C.+/2° C.
7. Count test organisms.
8. Calculate the number of organisms as colony forming units per ml (cfu/ml) of inoculum as follows:

$$\frac{cfu/\text{ml}(0.1\ \text{ml})}{9.9\ \text{gm}} = cfu/\text{gm of product}$$

B. Preparation of Test Samples:

1. Accurately pipette or weight 9.9 ml (gm) of product into an appropriately labeled or coded test tube or specimen cup.
2. Store test samples at ambient room temperature.

C. Inoculation and Plating of Samples:

1. Aseptically transfer 0.1 mil of the test organism into the appropriately labeled 9.9 ml (gm) sample of test material. Thoroughly mix or stir all samples.
2. Allow the samples to stand for six and twenty-four hours.
3. Remove one millileter or gram aliquots at the indicated times and transfer to 9.0 ml sterile DE Neutralizing broth.
4. Perform serial dilutions from $10^{-1}$ to $10^{-5}$ in duplicate.
5. Transfer 1.0 ml of each dilution into a 100 × 15 mm petri plate.
6. Overlay with approximately 20 ml of 45° C. Tryptic Soy Agar with lecithin and tween 80.
7. Gently swirl plates and allow solidify.
8. Incubate plates for 24-48 hours at 35° C.+/2° C. for aerobic organisms and an additional 2-4 days at 25° C.+/2° C., D. Sample Evaluation:

1. Read plates and record results on appropriate data sheet.
2. Using the calculated inoculum concentration for each test microorganism, calculate the log reduction for each microorganism to determine kill rate.

E. Records and Reports:

1. The laboratory will maintain a permanent copy of the recorded data for a period of no less than three years.
2. A written report will be issued upon completion of the study.

Results:

| Organisms | Inoculum Level | Average | Log Reduction |
|---|---|---|---|
| C. albicans 6 Hours | 1.47 × 10⁶ | 948 | 3.19 |
| C. albicans 24 Hours | 1.47 × 10⁶ | 220 | 3.82 |
| MR S. aureus 6 Hours | 1.36 × 10⁶ | 750,000 | 0.26 |
| MR S. aureus 24 Hours | 1.36 × 10⁶ | No Growth | 6.13 |
| A. niger 6 Hours | 3.31 × 10⁵ | 22,000 | 1.18 |
| A. niger 24 hours | 3.31 × 10⁵ | 210 | 3.20 |

Under the conditions of this study, the test article demonstrated reduction of growth and killing of medically important organisms within 24 hours.

Comparison of Compositions

| Mole ratio of silver ions to chloride ions | Kill rate/Log reduction E. coli | Kill rate/Log reduction S. aureus | Kill rate/Log reduction P. aeruginosa |
|---|---|---|---|
| Greater than 1 | 5.93 | 6.09 | 5.61 |
| Less than 1 | 2.84 | −0.55 | 5.66 |

Biocompatibility Test

A study was conducted in the guinea pig to evaluate the potential for delayed dermal contract sensitization of a test article. The study was conducted based on the requirements of the International Organization for Standardization 10993: Biological Evaluation of Medical Devices, Part 10: Tests for Irritation and Delayed-Type Hypersensitivity.

The test article was occlusively patched for 6 to 8 hours to the intact skin for ten guinea pigs, three times a week, for a total of nine induction treatments over a 3 week period. The control article was similarly patched to five guinea Pigs. Following a recovery period, the ten test and five control animals received a challenge patch of the test article. All sites were observed for evidence of dermal reactions at 24 and 48 hours after patch removal.

Under the conditions of this study, the test article showed no evidence of causing delayed dermal contract sensitization in the guinea pig.

What is claimed is:

1. An antimicrobial composition comprising: (a) anion donating salt; (b) silver ion donating salt; (c) at least 80% water as a solvent; and (d) hydrophilic polymer wherein the mole ratio of equivalents of silver ion donating salt to equivalents of anion donating salt in the composition is greater than 1, the composition having a silver content ranging from 0.0001 and 0.01 mole/liter and comprising silver salt particles and free silver ions.

2. The composition according to claim 1, wherein the silver ion donating salt is selected from the group consisting of silver nitrate, silver acetate, silver citrate, and silver sulfate.

3. The composition according to claim 1, further comprising one or more active agents.

4. The composition according to claim 3, wherein the one or more active agents are selected from the group consisting of antimicrobials, antibiotics, antivirals, enzymes, proteins and growth factors.

5. An antimicrobial composition comprising: (a) anion; (b) silver ion; (c) at least 80% water as a solvent; and (d) hydrophilic polymer wherein the mole ratio of equivalents of silver ion to equivalents of anion in the composition is greater than 1, the composition having a silver content ranging from 0.0001 and 0.01 mole/liter and comprising silver salt particles and free silver ions.

6. The composition according to claim 5, further comprising one or more active agents.

7. The composition according to claim 6, wherein the one or more active agents are selected from the group consisting of antimicrobials, antibiotics, antivirals, enzymes, proteins and growth factors.

* * * * *